United States Patent
Maurer et al.

(10) Patent No.: US 10,391,227 B2
(45) Date of Patent: *Aug. 27, 2019

(54) MEDICO-TECHNICAL MEASURING DEVICE AND MEASURING METHOD

(71) Applicant: Novalung GmbH, Heilbronn (DE)

(72) Inventors: Andreas Maurer, Tübingen (DE); Sven Filipon, Heilbronn (DE); Matthias Beurer, Stuttgart (DE)

(73) Assignee: Novalung GmbH, Heilbronn (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/301,143

(22) PCT Filed: May 15, 2015

(86) PCT No.: PCT/EP2015/001001
§ 371 (c)(1),
(2) Date: Sep. 30, 2016

(87) PCT Pub. No.: WO2015/172891
PCT Pub. Date: Nov. 19, 2015

(65) Prior Publication Data
US 2017/0021084 A1    Jan. 26, 2017

(30) Foreign Application Priority Data
May 15, 2014 (EP) .................... 14001728

(51) Int. Cl.
*A61B 5/00* (2006.01)
*A61M 1/36* (2006.01)
(Continued)

(52) U.S. Cl.
CPC ....... *A61M 1/3639* (2013.01); *A61B 5/14542* (2013.01); *A61B 5/6866* (2013.01);
(Continued)

(58) Field of Classification Search
CPC .............. A61M 1/3639; A61M 1/3641; A61M 1/6866; A61M 1/3663; A61B 5/14542; A61B 5/145
See application file for complete search history.

(56) References Cited

U.S. PATENT DOCUMENTS 3,418,853 A * 12/1968 Curtis ................ A61M 1/3639
600/488
4,194,974 A 3/1980 Jonsson
(Continued)

FOREIGN PATENT DOCUMENTS

CN        1913825 A       2/2007
DE        29810331 U1     9/1998
(Continued)

OTHER PUBLICATIONS

Benchoff, B., "Injection Molding With Hot Glue", Hackaday, May 12, 2014, one page.

*Primary Examiner* — Harshad R Patel
*Assistant Examiner* — Tran M. Tran
(74) *Attorney, Agent, or Firm* — Dinsmore & Shohl LLP (57) ABSTRACT

A medico-technical measuring device for measuring a property of a fluid, such as pressure for pressure measurement, includes a line extending along a central longitudinal axis to guide a fluid, such as blood, within a longitudinal cavity delimited by a wall. A sensor unit has a sensor and measures a property of the fluid guided in the longitudinal cavity. The line is provided with a radial cavity inserted in the wall in a radial direction, in which the sensor unit is at least partially arranged, and which is integrated in the wall such that the sensor is in communication with the fluid. In this way, a measuring device can be provided that allows simple handling—in particular, in combination with a comparatively precise measurement—especially, pressure measurement.

(Continued)

The measuring device may be produced according to a method and the measuring device may be used in a measuring method.

16 Claims, 4 Drawing Sheets

(51) Int. Cl.
*A61B 5/145* (2006.01)
*G01L 19/00* (2006.01)
*G01L 19/06* (2006.01)

(52) U.S. Cl.
CPC ...... *G01L 19/0023* (2013.01); *G01L 19/0654* (2013.01); *A61M 2205/3327* (2013.01); *A61M 2207/00* (2013.01)

(56) References Cited

U.S. PATENT DOCUMENTS

| | | | |
|---|---|---|---|
| 4,263,808 A * | 4/1981 | Bellotti | A61M 1/3639 73/714 |
| 4,425,918 A | 1/1984 | Moll et al. | |
| 4,431,009 A * | 2/1984 | Marino, Jr. | A61B 5/0215 600/486 |
| 4,443,407 A * | 4/1984 | Weinberg | G01N 33/4915 422/81 |
| 4,734,184 A | 3/1988 | Burleigh et al. | |
| 4,924,872 A * | 5/1990 | Frank | A61B 5/0215 600/486 |
| 5,105,820 A * | 4/1992 | Moriuchi | A61B 5/0215 600/486 |
| 5,148,811 A * | 9/1992 | Messinger | A61B 5/0215 600/486 |
| 5,237,999 A * | 8/1993 | von Berg | A61B 5/0235 600/486 |
| 5,351,686 A * | 10/1994 | Steuer | A61B 5/14535 600/310 |
| 5,370,123 A * | 12/1994 | Shinzato | A61B 5/0215 600/486 |
| 5,387,329 A | 2/1995 | Foos et al. | |
| 5,581,038 A * | 12/1996 | Lampropoulos | A61B 5/0215 73/721 |
| 5,614,677 A | 3/1997 | Wamsiedler et al. | |
| 5,925,830 A * | 7/1999 | Schalk | G01F 1/584 73/861.08 |
| 5,965,089 A * | 10/1999 | Jarvik | A61M 1/101 422/44 |
| 6,101,406 A * | 8/2000 | Hacker | A61B 5/14557 356/39 |
| 6,136,136 A | 10/2000 | Heider | |
| 6,272,930 B1 | 8/2001 | Crozafon et al. | |
| 6,725,726 B1 * | 4/2004 | Adolfs | A61B 5/0215 73/756 |
| 6,880,404 B2 * | 4/2005 | Uberreiter | A61M 1/3639 73/706 |
| 6,887,214 B1 * | 5/2005 | Levin | A61M 1/3639 210/645 |
| 7,025,750 B2 * | 4/2006 | Brugger | A61M 1/3621 604/246 |
| 7,059,195 B1 * | 6/2006 | Liu | A61B 5/02152 73/753 |
| 7,108,672 B2 * | 9/2006 | Steele | A61M 1/3624 210/782 |
| 7,313,968 B2 * | 1/2008 | Kaneko | A61M 1/3639 73/706 |
| 7,410,473 B2 * | 8/2008 | Levin | A61M 1/3639 210/645 |
| 7,748,275 B2 * | 7/2010 | Kouda | A61M 1/3641 604/7 |
| 7,771,380 B2 * | 8/2010 | Jonsson | A61M 1/3639 210/645 |
| 7,856,887 B2 * | 12/2010 | Klees | G01L 9/0026 600/488 |
| 7,879,241 B2 * | 2/2011 | Sparks | A61M 1/1656 210/321.71 |
| 7,921,723 B2 * | 4/2011 | Reiter | G01L 19/0023 73/714 |
| 8,506,684 B2 * | 8/2013 | Weaver | A61M 1/3627 604/5.04 |
| 8,721,883 B2 * | 5/2014 | Lauer | A61M 1/1037 210/240 |
| 9,186,072 B2 * | 11/2015 | Manstrom | A61M 5/007 |
| 9,551,625 B2 * | 1/2017 | Brugger | G01L 9/0041 |
| 9,808,567 B2 * | 11/2017 | O'Mahony | A61M 1/3639 |
| 9,883,888 B2 * | 2/2018 | Frey | A61B 17/3468 |
| 2002/0073782 A1 * | 6/2002 | Chevallet | A61M 1/3639 73/700 |
| 2004/0039290 A1 * | 2/2004 | Narimatsu | A61B 5/02141 600/490 |
| 2005/0284815 A1 | 12/2005 | Sparks et al. | |
| 2007/0261496 A1 | 11/2007 | Jonsson et al. | |
| 2010/0114063 A1 * | 5/2010 | Recinella | A61M 25/0097 604/508 |
| 2012/0258545 A1 | 10/2012 | Ash et al. | |
| 2014/0076058 A1 | 3/2014 | Brugger et al. | |

FOREIGN PATENT DOCUMENTS

| | | |
|---|---|---|
| DE | 102013012433 A1 | 1/2015 |
| EP | 0330891 A1 | 9/1989 |
| EP | 0688531 A1 | 12/1995 |
| EP | 0762084 A2 | 3/1997 |
| EP | 0993266 A1 | 4/2000 |
| JP | H03258235 A | 11/1991 |
| JP | 2005311321 A | 11/2005 |
| JP | 2008296061 A | 12/2008 |
| JP | 2009200172 A | 9/2009 |
| JP | 2011222782 A | 11/2011 |
| JP | 2014032190 A | 2/2014 |
| WO | WO-1997015228 A1 | 5/1997 |
| WO | 2012127422 A1 | 9/2012 |

* cited by examiner

MEDICO-TECHNICAL MEASURING DEVICE AND MEASURING METHOD

CROSS-REFERENCE TO RELATED APPLICATIONS

This application is the U.S. national phase of international application No. PCT/EP2015/001001, filed May 15, 2015, which claims priority to European application No. EP 14001728.6, filed May 15, 2014, each of which are incorporated herein in their entirety.

FIELD OF THE INVENTION

The present invention relates to a medico-technical measuring device for measuring a property of a fluid—in particular, for pressure measurement—comprising a line extending along a central longitudinal axis and configured to guide a fluid—in particular, blood—within a longitudinal cavity delimited by a wall, and a sensor unit having a sensor, which sensor unit is configured to measure a property of the fluid guided in the longitudinal cavity.

The present invention further relates to a method for producing the medico-technical measuring device, comprising the steps of providing a line with a wall and arranging a sensor in the line. The present invention relates to a medico-technical measuring device with individual characteristics as disclosed herein, as well as a production method or a measurement method each with individual characteristics as disclosed herein.

BACKGROUND OF THE INVENTION

Measuring devices and sensors are known which are arranged on a connector, adapter, or spacer between individual sections of a line. The line guides a fluid—in particular, an isotonic saline solution or other crystalloid infusion solutions or blood—the property of which—in particular, pressure—is to be recorded. In such measuring devices, there is often the risk of coagulation (or so-called blood clotting) or hemolysis—in particular, as a result of edges, undercuts, or fluidically unfavorable transitions. The connecting elements or connectors also increase the risk of leakages—in particular, on interfaces between a connector and an extra-corporeal hose kit or in the measuring system—and must be additionally checked. In particular, the problem is known from practice that leakages can occur, e.g., on Luer connections. Especially in the case of extra-corporeal circulation, there is then the risk that air can potentially be sucked into a discharge line, in which there can be a low pressure, and mixed with the fluid/blood. From a feed line in which there can be an overpressure, there is the potential for fluid/blood to be squeezed out of the line. In this case, the sterility of the overall device can no longer be ensured. In addition, the connector or adapter must be mounted on the line, and a seal, bonded joint, or other interface, which is as sterile as possible or which can be sterilized, must be able to be ensured.

As an alternative to such measuring devices or sensors coupled or integrated in the line, a measurement—in particular, a pressure measurement—can also be effected outside the line. The corresponding sensor can then directly record a pressure, e.g., by means of a water column. However, a so-called priming operation is required for this type of pressure measurement, in order to be able to start the pressure measurement. With priming, the hose system is filled with a crystalloid solution, such as isotonic saline solution (NaCl), after which the hose system is vented. There is a risk that the venting of the line/hose system will be carried out incorrectly. During the measurement, there is a risk that fluid/blood penetrating the crystalloid solution in a line leading to a measuring sensor might impair or interrupt the measuring process, which can be life threatening.

Also disadvantageous in this type of pressure measurement are measuring errors, which are caused by gas inclusions in the water column. Also, in most cases, the pressure measurement itself can be performed only with a delay, since a pressure wave must first be transferred through the water. Therefore, such a direct pressure measurement makes it difficult, for example, to synchronize a pump with the arterial pressure curve of the patient.

The German patent application (Offenlegungsschrift) DE 10 2005 063 410 A1 describes a blood vessel catheter in which a blood pressure sensor is arranged on a housing which is coupled to a catheter tube.

The German patent application (Offenlegungsschrift) DE 10 2007 038 402 A1 describes a device for recording a pressure in which a sensor element is embedded in the wall structure of a line separate from a medium guided along the line.

The European patent specification EP 0 328 558 B1 describes an elastic hose on whose internal surface a coating is applied in which a pressure signal can be measured when the hose is deformed.

SUMMARY OF THE INVENTION

An aim of the present invention is to provide a medico-technical measuring device—in particular, a blood pressure measuring device—which facilitates easy handling—in particular, in conjunction with a comparatively exact measurement. The aim can also be described such that the medico-technical measuring device should have a simple construction and/or be able to minimize the risk of impurities or air inclusions or leakages.

The aim is accomplished by means of a medico-technical measuring device for measuring a property of a fluid—in particular, for pressure measurement—comprising
a line—in particular, a hose line—which extends along a central longitudinal axis and is configured to guide a fluid—in particular, blood—within a—in particular, cylindrical—longitudinal cavity delimited by a wall, and
a sensor unit having a sensor—in particular, a pressure sensor—which sensor unit is configured to measure a property of the fluid guided in the longitudinal cavity, wherein, with the measuring device according to the invention, it is provided for the line to have a radial cavity inserted in the wall in a radial direction, in which cavity the sensor unit is at least partially arranged and which is integrated in the wall such that the sensor is in communication with the fluid in the longitudinal cavity.

The arrangement of the sensor directly in the wall has metrological or also constructive advantages. The sensor can be easily arranged on a metrologically preferable position—in particular, in close proximity to a flow path of the fluid, or even directly in the flow path. In particular, the number of interfaces can also be reduced—especially, to just a single interface in the wall. The arrangement of the sensors integrated into the wall renders spacers, couplings, or other connections superfluous. For example, no Luer connections or other access points to the line are required. As a result of this, the risk of leaks or of any non-sterile interfaces is considerably reduced. However, with the spacers or adapters—in particular, Luer connections—most commonly used in prior art, there are always at least two or three interfaces—namely, the interface(s) between the spacer or adapter and the line on the one hand, and the interface between the spacer or adapter and the sensor on the other. Therefore, it is important to emphasize that a line within the meaning of the invention is, in particular, not a spacer, a connector, or an adapter. In addition, incorrect operation of any connections can be also be avoided. It can, for instance, be avoided that, for example, in an extra-corporeal line system or hose system (such as those used in dialysis, in heart or lung support, or with a cardiopulmonary bypass in cardiac surgery, or in a catheter or a sheath, e.g., in cardiology) in a section with negative pressure (in particular, with a pressure less than atmospheric pressure), air be drawn into the line/hose system or the catheter in the area of the pressure measurement arrangement, or that fluid/blood escape from the circulation in a section with positive pressure (in particular, at the point where fluid/blood is fed back into the body).

A priming process, especially in relation to the sensor, is thereby no longer necessary, which can save time and make the pressure measurement in certain (e.g., life-threatening) situations particularly useful. There are no longer any additional supply lines or hoses to be vented. In other words, the integrated arrangement of the sensors permits an "inline" measurement, without a time lag. The line/hose system (including a potentially provided catheter or cannula) guiding the blood can thereby be filled and vented independently of a pressure measurement.

In the last few years, sensors—in particular, pressure sensors—with ever smaller dimensions have become available. This now allows for an advantageous arrangement of the sensor in direct proximity to the fluid to be measured. The integrated sensor can be arranged directly in the fluid stream, without influencing the fluid stream. This also facilitates a particularly exact (pressure) measurement. In this connection, an integration, for example, can also be effected in a wall which has a wall thickness in the range of only 1 mm to 3 mm.

Such an arrangement of the sensor also facilitates a largely arbitrary selection of the position of the sensor on any section or any circumferential position along the line—in particular, a hose line. The sensor unit or the sensor can thereby form a part of the wall.

A measuring device (in particular, a pressure measuring device) thereby preferably means a device which can guide, or feed or discharge, a specific fluid in a specific state—in particular, in a flow state—and can record and, optionally, at least partially evaluate at least one property—in particular, the pressure of the liquid. The measuring device can preferably record and evaluate at least the pressure and, optionally, other physical or chemical variables as well. Such a measuring device can, for example, be used for an invasive pressure measurement or in conjunction with an extra-corporeal circulation, e.g., for renal replacement, cardiopulmonary support, or liver support. The advantages of good tightness and/or sterility can thereby ensue, especially with an invasive/implanted arrangement. By means of the measuring device, the vital functions, for example, of a patient can be monitored, e.g., heart muscle contractions (hemodynamics), or a loss of pressure caused by extra-corporeal circulation can be measured.

The measuring device can thereby comprise several different sensors. In addition to the sensor, the measuring device can have additional components, such as a protective cap, a female connector (for example, a four-pole female connector) or a preferably water-repellent membrane, wherein the membrane can ensure a protection of the sensor against external influences. The sensor can, for example, work on the basis of the differential pressure principle. The measuring device then preferably has a connection to the outside air or environment. The membrane can be attached to a sensor cover over the sensor and protect the sensor—in particular, the bonded electronic connections of the sensor. The membrane can prevent media (e.g., blood, water, isopropanol) from coming into contact with these sensor connections. The membrane is preferably hydrophobic on both sides, i.e., in both directions, wherein air can be allowed to pass through (preferably) unimpeded.

One property—in particular, a pressure—can thereby also be measured in several measurement positions, depending upon the medical application—in particular, a suction pressure in a first position upstream of a pump, a pump pressure in a second position downstream of the pump, and an additional one—especially, a reperfusion pressure—in a third position downstream of a membrane ventilator. In other words, the measuring device can optionally have a plurality of sensor units, or at least a plurality of sensors. Accordingly, the line (including any catheter or cannula present) can also have a plurality of radial radial cavities.

A fluid thereby preferably means a liquid; however, the fluid can also be a gas, or at least have gaseous components.

By line is thereby preferably meant any type of line which can be used in conjunction with medical care, diagnosis, or therapy, e.g., also in conjunction with any catheters. The line can be part of a medical instrument or set of instruments. The—in particular—blood-guiding line can be part of a so-called hose set or can form this hose set. The (hose) line can thereby also comprise a cannula, ensuring access to the body, or be designed in sections as a cannula. The line is preferably flexible, i.e., elastically pliable. In particular, the line can be curved or bent. The elasticity of the line is thereby not—or not noticeably—influenced by the sensor unit. To a great extent, the diameter of the line can be freely selected. In particular, internal diameters of, for example, 9.52 mm (⅜") or 6.35 mm (¼") are appropriate.

The wall, or even the entire line, can be designed from a flexible plastic material—in particular, from polyvinyl chloride (PVC) material. In the simplest case, the line is, for example, a PVC hose frequently used in medical technology. The plastic material is preferably a high-purity, non-phthalate soft PVC. Thereby, a wall thickness of the wall and/or line is, for example, in the range of 1 mm to 5 mm—preferably in the range of 1.2 mm to 3.5 mm, more preferably in the range of 1.5 mm to 3 mm, and particularly in the range of 1.6 mm to 2.4 mm.

A sensor unit thereby preferably means a component of the measuring device by means of which a measuring signal—in particular, a pressure signal—can be recorded and either processed or at least transmitted.

A sensor (in particular, pressure sensor) thereby preferably means a component of the measuring device by means of which a property of a fluid can at least be recorded by a measuring signal—in particular, a pressure signal. A property or a state of the fluid can thereby be recorded—for example, through a physical or chemical variable. A property can, for example, be described by a specific portion of a gaseous component, for example, a portion by volume of $CO_2$ or $O_2$. In so doing, the sensor can, for example, be configured to measure the infusion pressure or injection pressure in fluid-guiding medical devices. For example, a piezo-resistive sensor can be used. Alternatively, sensors can also be used which are based upon one or more of the following physical principles or operating modes: for example, piezoelectric, capacitive, inductive, frequency-dependent, or sensors with Hall element, fiber optic sensor. The sensor can thereby be inserted into the inner lumen of the line on its surface facing the blood, such that a continuous and smooth transition between the sensor and the inner lumen is ensured—in particular, to prevent coagulation or hemolysis in the area of the sensor.

A radial cavity thereby preferably means a recess introduced or provided in a radial direction, a bore, a cavity, or a hollowed-out area or section, or take-up volume. The radial cavity can also be formed by a longitudinal cavity extending in a radial direction, which is only accessible from one side of the wall. The radial cavity need not necessarily be a duct or a hole in the wall.

An opening preferably means an aperture or a radial cavity which completely breaks through the wall, i.e., is provided continuously through the wall.

A recess preferably means a cavity extending in a radial direction from an inner side of the wall, i.e., an inner sleeve surface, which need not necessarily run up to an external sleeve surface of the wall. In other words, the recess is not necessarily a hole in the wall, but can hollow out the wall—also just in sections—in a radial direction.

An arrangement "in communication with" thereby preferably means an arrangement in which the sensor is in direct contact with the fluid. The sensor can be arranged in the fluid stream or on the side of the fluid stream or on the side of a flow path of the fluid stream.

According to an embodiment example, the measuring device is configured to link the sensor unit in an individual (in particular, geometric) interface with the line—in particular, to attach/fix it directly to an external sleeve surface of the wall, thereby positioning it. As a result, the risk of leakages can be reduced—in particular, in comparison with adapters or spacers which have several interfaces. In other words, the measuring device need have only one single interface or one single attachment point or access point via which the sensor can be integrated in the line.

The sensor unit can be integrated in the line on the single interface between the sensor unit and the line. The interface is thereby preferably formed solely by the radial cavity or by the radial cavity and an external sleeve surface of the wall.

An interface thereby preferably means a surface on which the sensor unit can be connected to the wall. The interface can thereby also comprise different surfaces, which are, however, preferably arranged in the same area of the wall—in particular, adjacent to one another.

According to one embodiment example, the sensor is arranged in a radial position between an/the external sleeve surface and an internal sleeve surface of the wall inside the wall distanced from the external sleeve surface—in particular, in a section which is arranged closer to the internal sleeve surface than to the external sleeve surface. As a result, the sensor can be arranged close to the flow path of the fluid, or even in the flow path, which facilitates a comparatively precise "inline" measurement.

According to one embodiment example, the sensor or a free end of the sensor unit projecting radially inwards is arranged at least approximately flush with an/the internal sleeve surface of the wall. Favorable flow conditions can be ensured as a result. Swirls caused by undercuts or edges can largely be prevented. This means that a risk of blood clots or hemolysis can also be reduced.

The sensor can thereby be arranged in a radial position, which at least approximately corresponds to a radial distance of an internal sleeve surface of the line to the central longitudinal axis in the area of the radial cavity. In other words, the sensor can be arranged in a radial position which is characterized by a radial distance to the central longitudinal axis corresponding to half the diameter, i.e., the radius of the longitudinal cavity. The sensor can delimit the longitudinal cavity in a radial direction.

According to one embodiment example, the radial cavity is an opening—in particular, a cylindrical bore with a uniform diameter. This ensures a particularly simple construction. An opening can easily be introduced into the wall at any time thereafter, and also in any position. Furthermore, the sensor can be positioned in the radial cavity from outside.

According to one embodiment example, an internal surface of the radial cavity is cylindrical or conical, or has a polygonal cross section. At the same time, the radial cavity is not necessarily round or circular, but can have any cross section. Where it has a round or circular geometry, the radial cavity can be easily sealed—in particular, by means of an oversize fit.

According to one embodiment example, a diameter or an extent of a cross section of the radial cavity is smaller than a section of the sensor unit—in particular, of the sensor as well—that corresponds geometrically thereto. The individual interface can thus, to a large extent, be sealed independently of any substance-to-substance connection. A substance-to-substance connection is not necessary in the area of the internal surface of the radial cavity. At the same time, the radial cavity can, together with the sensor unit and/or the sensor, form an oversize fit to which the wall can be sealed fluid-tight. In other words, a corresponding geometry can ensure the fluid-tightness of the radial cavity between the sensor and the wall, even if no adhesive agent, adhesive, or the like is provided for on this interface.

The radial cavity is preferably circular. This facilitates an exact-fit arrangement of the sensor unit in the radial cavity—in particular, independently of a specific rotation position.

An oversize fit thereby preferably means an interface at which one of the components to be coupled has a specific measurement through which it can be ensured that the two components to be coupled can only be connected to one another where they are geometrically aligned on top of each other, and that a gap-free connection, free of play, is ensured.

A diameter or an extent of a cross section of the radial cavity is thereby in the range, for example, of 1 mm to 5 mm—preferably in the range of 2 mm to 4 mm, more preferably in the range of 2.5 mm to 3.5 mm, and particularly in the range of 3 mm to 3.3 mm—especially 3.15 mm. According to a variant, the sensor unit then has a radial section which has a diameter or an extent in the range of 1 mm to 5 mm—preferably in the range of 2 mm to 4 mm, more preferably in the range of 2.5 mm to 3.5 mm, and particularly in the range of 3 mm to 3.3 mm—especially 3.1 mm—wherein the radial section forms an oversize fit—in particular, a press fit—with an internal surface of the radial cavity. A sealing of the radial cavity can thus result—in particular, also without any adhesive agent in the area of the radial cavity.

According to a special embodiment example, the wall has an at least approximately constant diameter and/or an at least approximately constant wall thickness. It can thus be ensured that the sensor can be positioned in a pre-definable radial position by means of the sensor unit, and, indeed, irrespective of which point on the wall the radial cavity is inserted at.

According to a special embodiment example, the sensor extends at least approximately across the entire cross section profile of the radial cavity and has at least approximately the same extent as a diameter or an extent of the radial cavity. The entire cross section of the radial cavity can thus be used for the measurement—in particular, the pressure measurement. In other words, the radial cavity can have a comparatively small design. In particular, the radial cavity can have a diameter which is only as big as or only slightly larger than is required for the measurement.

According to a special embodiment example, the sensor and/or the sensor unit has a front surface which is arranged radially flush to an internal sleeve surface of the line, wherein the front surface further forms the wall—in particular, across the entire cross section surface of the radial cavity. A transition between the internal sleeve surface and the radial cavity can thus be formed, so that undercuts or edges, and the swirls or dead spaces potentially concomitant therewith, can be avoided to a great extent. Mention should also be made of the fact that the sensor does not extend into the line cross section. According to a special variant, the front surface is designed to correspond geometrically to the geometry of the internal sleeve surface—in particular, to be concavely curved. A shape-optimized integration can thus result. The sensor is thereby not at all "visible" for the blood stream. A risk of swirls can be as good as ruled out.

According to one embodiment example, the sensor unit is configured to position the sensor in a predefined radial position in the radial cavity—in particular, by the fact that the sensor unit is designed in a section configured for it geometrically corresponding to an external sleeve surface of the line/wall. For this purpose, the sensor unit can be designed, at least in sections, such that the sensor unit can be positioned in a predetermined relative position directly on the wall. The radial position of the sensor can thus be predetermined by geometrical configuration of the sensor unit. For example, the assembly of the sensor in the "correct" position can thereby also be simplified. For example, the sensor unit need only be arranged on the external sleeve surface—in particular, in a longitudinal alignment corresponding to the central longitudinal axis.

According to one embodiment example, the sensor unit has an abutting section which is designed to geometrically correspond to an/the external sleeve surface of the wall in at least the area of the radial cavity—in particular, circumferentially around the radial cavity. The sensor unit can thus be easily and robustly connected to the line and can, in particular, be affixed to the line in the area of the radial cavity circumferentially around the radial cavity. The abutting section has, for example, a concave contour which is designed to geometrically correspond to a convex contour of the line or wall.

The abutting section is thereby preferably configured to define the radial position of the sensor—namely, via the external sleeve surface of the wall. In other words, a radial extension of a sensor mounting or of a radial section of the sensor unit is adapted to the geometry of the abutting section such that, when the abutting section lies flat on the external sleeve surface of the wall, the sensor is arranged in a predetermined radial position—in particular, within the radial cavity.

An abutting section thereby preferably means a flat section on which the sensor unit can abut against the line. The abutting section is also preferably inherently stable, i.e., not elastically or plastically deformable, so that a relative movement between the line and the abutting section can be avoided in the area of the radial cavity. This can ensure a permanent, reliable connection between these two components.

In an advantageous embodiment of the invention, the sensor unit is partially arranged in the radial cavity in the wall and integrated in the wall such that the sensor is in communication with the fluid, and the abutting section of the sensor unit is designed circumferentially around the radial cavity and geometrically corresponds to an/the external sleeve surface of the wall.

The sensor unit, therefore, has a part, i.e., the sensor or at least a part of the sensor, which is located in the radial cavity in the wall of the line and another part which is arranged externally on the line and can be moved across the flat section to abut against the external wall of the line. By means of the substance-to-substance connection of the flat section or of the abutting section of the sensor unit around the sensor in the radial cavity, an optimum sealing of the line is ensured to the outside. Alongside the substance-to-substance fixation of the sensor unit to the line, by means of the protrusion of the sensor into the radial cavity, a mechanical fixation—in particular, with regard to tensile forces in the direction of the longitudinal extension of the line—is also ensured.

According to one embodiment example, the sensor unit has an abutting section which, at least in the area of the radial cavity—in particular, circumferentially around the radial cavity—is connected substance-to-substance with an/the external sleeve surface of the line or wall—in particular, by means of an adhesive agent. The sensor unit can thus be affixed to the line in a robust way. The substance-to-substance connection in the area of the external sleeve surface also has the advantage that any adhesive agent—in particular, glue—does not necessarily have to be provided on an internal surface of the radial cavity. It can thus be avoided that the fluid—especially, blood—comes into contact with the adhesive agent. The adhesive agent is preferably flexible and moisture resistant. The adhesive agent is preferably constituted so as to ensure a permanent adhesive connection to plastic—especially, PVC. The adhesive agent is preferably a curing glue.

For example, the abutting section in the area of the radial cavity is connected circumferentially around the radial cavity with the external sleeve surface by means of the adhesive agent, wherein the sensor unit abuts exactly and fluid-tight directly against an internal surface of the radial cavity, without an adhesive agent. On the one hand, a relatively robust, durable flat connection is thereby ensured between the line and the abutting section. On the other hand, it can be effectively avoided that the line is twisted relative to the sensor unit.

It should be noted that an exclusive arrangement of the sensor and the sensor unit in the radial cavity of a flexible or elastic line can be problematic, since leakages can easily occur if the flexible or elastic line moves or is moved, while the sensor, or the sensor unit, provided as a rigid component, is arranged rigidly in the radial cavity and cannot move in line with this movement. It could, therefore, result in leakages in the substance-to-substance connection of the sensor unit in the cavity to the wall of the line.

According to one embodiment example, the sensor unit has a radial section in which the sensor is arranged, wherein the radial cavity preferably has an extension in a radial direction, which is preferably larger than half of a wall thickness of the wall in a section in which the radial cavity is arranged. The sensor can thus be arranged by means of the radial section in a predefined position in the radial cavity—in particular, in a comparatively exact way in an exactly pre-definable radial position, e.g., exactly at the height of the internal sleeve surface of the wall. According to one variant, the radial extension can correspond at least approximately to the wall thickness, so that the sensor can be positioned almost in the flow path, i.e., almost at the same radial distance from a central longitudinal axis of the line as the internal sleeve surface of the wall. The radial section can thereby be adapted to the wall thickness. In other words, the position of the sensor can be set/defined by a predetermined radial extension of the radial section.

A radial section thereby preferably means a section extending in a radial direction which is configured to be coupled to the radial cavity and which is designed in cross section to geometrically correspond to the cross-sectional profile of the radial cavity. The radial section can thereby comprise a sensor mounting which is configured to hold or affix the sensor to the sensor unit. A sensor mounting thereby preferably means a part of the sensor unit on which the sensor (or a quite specific type of sensor) can be positioned on the sensor unit, insofar as the sensor is not integrated in the sensor unit or formed by the sensor unit. The sensor mounting can thereby also have, for example, electrical contacts by means of which the sensor is in electrical contact with a cable or any communication interface or energy supply. The radial section can thereby also be formed at least sectionally by the sensor mounting.

According to one embodiment example, the sensor unit, at least partially—or at least a/the radial section of the sensor unit—is designed from a plastic material. An interface to the wall can thus be provided which can also be effectively sealed—in particular, with PVC hoses. An abutting section of the sensor unit can also thereby be effectively connected to the wall (advantageous material pairing).

According to one embodiment example, the measuring device is a disposable device provided for one-time use, wherein the sensor unit preferably has a coupling point for a communication and/or energy supply—in particular, for a transmission by wire over a cable or for a wireless transmission. The integration of the sensor in the wall facilitates a measuring device of simple design, in which, for example, only a cable or a stick must be removed before the measuring device is disposed of.

According to one embodiment example, a measuring system for extra-corporeal circulation with at least two measuring devices according to the invention can be created, wherein one of the measuring devices has a feed line and another of the measuring devices has a discharge line. In this way, a property—in particular, a pressure of a discharged fluid, as well as of a fed fluid—in a circulation can be measured. In so doing, in the discharge line in particular, the risk (especially, on any Luer connections) that air be drawn into the line, can be reduced. In the discharge line, the risk, in particular, that (especially on any Luer connections) the fluid (in particular, blood) be pressed out or spurt out in the event of an over pressure, can be reduced. In other words, the integration of the sensors in the wall has the advantage that leakages can largely be ruled out. The number of interfaces can be reduced—in particular, to a single interface per line.

The aim is also accomplished by a method for producing a medico-technical measuring device—in particular, a medico-technical measuring device according to the invention—comprising the steps:

providing a line with a wall—in particular, a flexible, pliable hose line;

arranging a sensor in the line;

for which it is envisaged according to the invention that a radial cavity be inserted in the wall in a radial direction and the sensor be arranged in the radial cavity—in particular, in a radial position between an external sleeve surface and an internal sleeve surface of the wall at a distance from the external sleeve surface. Thus result, in particular, the advantages explained in connection with the measuring device.

According to one embodiment example of the method, the measuring device is connected substance-to-substance with an external sleeve surface of the wall, and/or the sensor in the radial cavity is positioned fluid-tight in an oversize fit in the wall. A measuring device can thus be provided which has a single, comparatively robust, and durable interface which can be sealed fluid-tight with good reliability. The seal preferably takes place in the radial cavity alone, and the distinct, relative position can preferably be ensured by the substance-to-substance connection. A substance-to-substance connection can thereby increase the robustness.

The aim is also accomplished by a method for measuring by means of a medico-technical measuring device—in particular, for pressure measurement by means of a medico-technical measuring device according to the invention—comprising the steps:

guiding a fluid—in particular, blood—through a line within a longitudinal cavity delimited by a wall—in particular, through a hose line;

measuring a property of a fluid by means of a sensor of the measuring device;

for which it is envisaged according to the invention that the sensor be positioned in a radial cavity inserted in the wall, and the property be measured in the radial cavity—in particular, in a radial position between an external sleeve surface and an internal sleeve surface of the wall at a distance from the external sleeve surface. The measurement—in particular, pressure measurement—can ensue "inline" within the wall. The integrated arrangement of the sensors permits an "inline" measurement without a time lag.

DETAILED DESCRIPTION OF THE DRAWINGS

Figure 1:
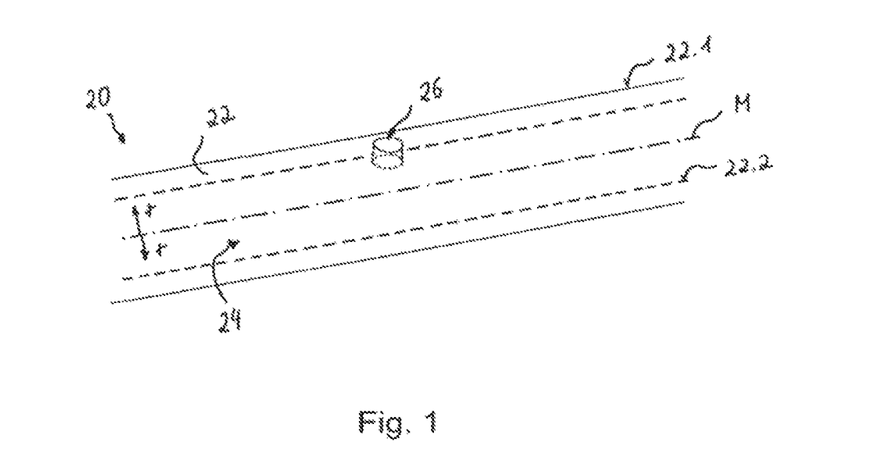
FIG. 1 is a perspective view in a schematic representation of a line of a medico-technical measuring device according to one embodiment example of the invention.

In connection with the description of the following figures, reference is made to the embodiment example in FIG. 1 for reference signs which are not explicitly explained.

FIG. 1 shows a line 20 in the form of a hose line which has a wall 22. The line 20 can be designed from an elastic material and be flexible or pliable. The wall 22 has an external sleeve surface 22.1 and an internal sleeve surface 22.2. The wall 22 or the internal sleeve surface 22.2 delimits a longitudinal cavity 24, in which a fluid—in particular, blood—can be guided. The line 20 extends in a longitudinal direction along a central longitudinal axis M. A radial cavity 26 is inserted in the wall 22 in a radial direction r. The radial cavity 26 is a radial opening in the form of a hole, which extends from the external sleeve surface 22.1 to the internal sleeve surface 22.2 and forms a passage. A sensor or a sensor unit can now be positioned in this passage, and a seal can thereby ensue by means of the sensor or the sensor unit, as is explained in connection with the following figures.

Figure 2:
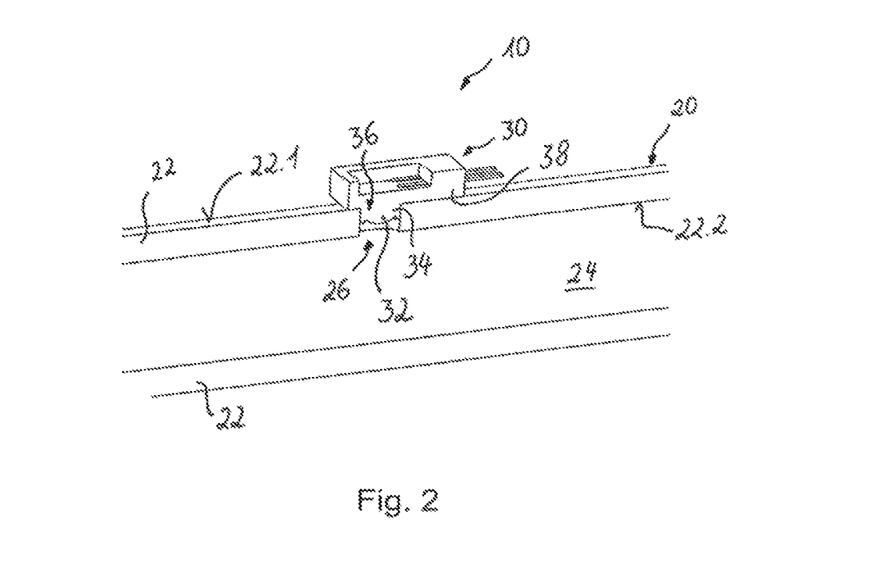
FIG. 2 is a perspective view in a schematic representation of a sensor unit of a medico-technical measuring device according to one embodiment example of the invention in an arrangement on the line shown in FIG. 1.

FIG. 2 shows a medico-technical measuring device 10 which has the line 20 and a sensor unit 30 described in FIG. 1. A sensor 32 is arranged in or on the sensor unit 30. The sensor 32 can be interpreted as a component of the sensor unit 30. The sensor 32, or, at least partially, the sensor unit 30 also, is arranged in the radial cavity 26, wherein the sensor 32 is positioned between the external sleeve surface 22.1 and the internal sleeve surface 22.2. The sensor unit 30 has a radial section 36 extending in a radial direction and an abutting section 38 extending in a longitudinal direction. The radial section 36 comprises a sensor mounting 34, in which the sensor 32 is arranged. The sensor mounting 34 and/or the sensor 32 are designed to geometrically correspond to the radial cavity 26. The abutting section 38 abuts against the external sleeve surface 22.1—in particular, flat circumferentially around the radial cavity 26.

Figure 3:
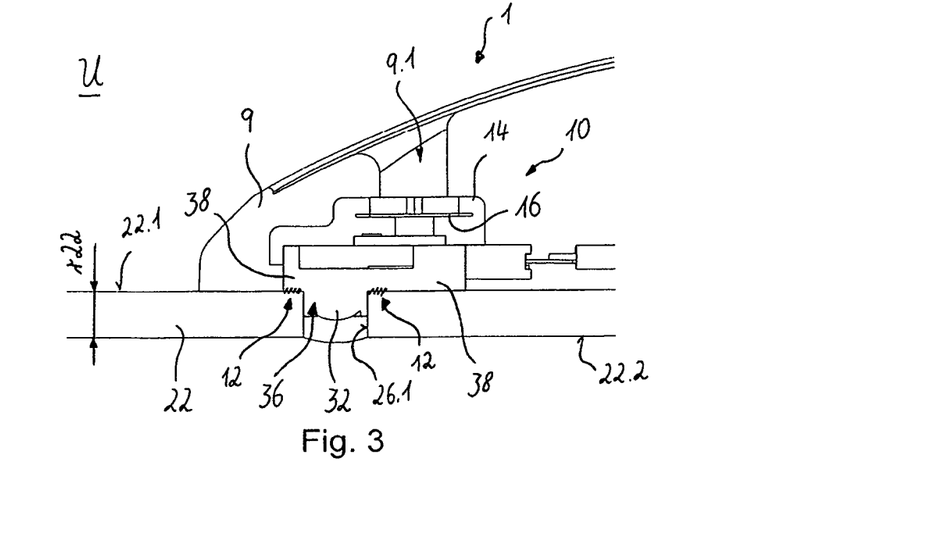
FIG. 3 is a side view in a schematic representation of a medico-technical measuring device according to one embodiment example of the example.

FIG. 3 shows a medico-technical measuring system 1, which comprises inter alia the medico-technical measuring device 10 depicted in FIG. 2, as well as an extrusion 9 with a passage 9.1, wherein the sensor 32 is in communication with the environment U via the passage 9.1. The sensor 32 is covered by a cover 14 and protected by an air-permeable, water-repellent membrane 16. FIG. 3 shows in detail that the radial section 36 abuts in an exactly flat manner against an internal surface 26.1 of the radial cavity 26—in particular, circumferentially—in order to be able to ensure a sealing of the longitudinal cavity. However, the abutting section 38 contacts only the external sleeve surface 22.1 and, in fact, in sections—directly and/or, optionally (as indicated), indirectly via an adhesive agent 12. The adhesive agent 12 is preferably provided completely circumferentially around the radial cavity 26 on the external sleeve surface 22.1 and/or the abutting section. However, the adhesive agent 12 is not provided on the internal surface 26.1—in particular, to be able to avoid contact with the fluid guided in the longitudinal cavity.

The radial position of the sensor 32 explained by means of FIG. 3 is given only as an example. The radial position of the sensor 32 can deviate from the position shown. In particular, the sensor 32 can be arranged further inside closer to the internal sleeve surface 22.2, which can provide advantages in many applications, e.g., advantages of a direct "inline" measurement in the flow path, i.e., at least almost without the influence of any flow swirls on any undercuts or edges.

The wall 22 has a wall thickness r22, which is, for example, in the range of 1 mm to 5 mm—in particular, in the range of 1.6 mm to 2.4 mm. The radial position of the sensor 32 is at least approximately central in relation to the external and internal sleeve surfaces 22.1, 22.2. The radial section 36 can, however, have a larger radial extension than shown. In particular, the radial section 36 can have a radial extension which is in the range of the wall thickness r22.

Figure 4:
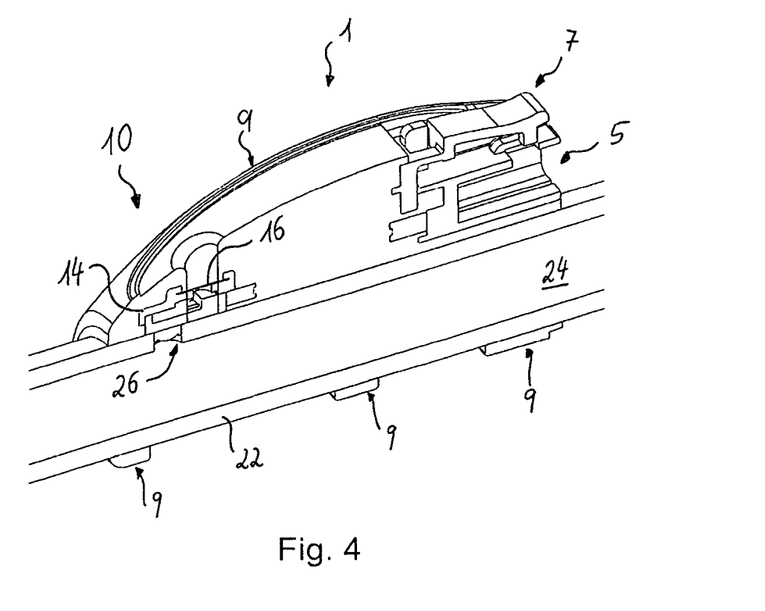
FIGS. 4 and 5 are different perspective sliced views in a schematic representation of the medico-technical measuring device shown in FIG. 3.
Figure 5:
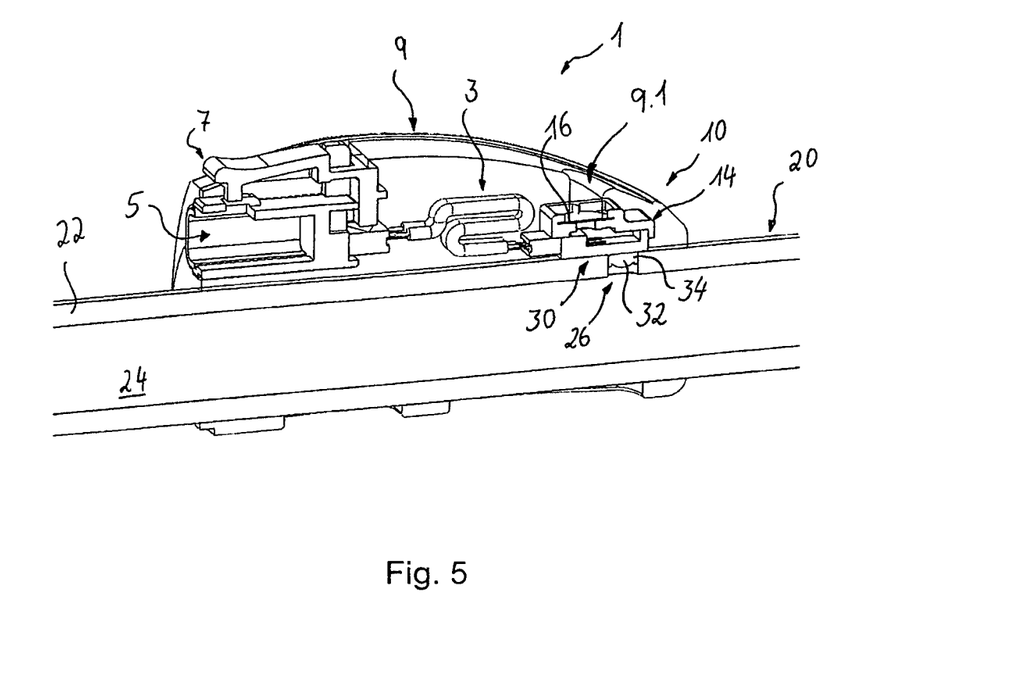

FIGS. 4 and 5 show further components of the measurement system 1—in particular, a female plug 5—which provides a coupling point for a communication and/or energy supply, and a button 7 for manual operation of the measurement system 1. The female plug 5 is connected to the sensor unit 30 and the sensor 32 by means of an adapter cable 3, which is arranged in the extrusion 9.

The female plug 5 shown in FIG. 5 is configured to accommodate either a plug in conjunction with an (external) cable or a type of "stick" or module. The stick can ensure wireless communication, e.g., via WLAN, radio, or Bluetooth. The stick can also have an energy supply, e.g., a battery. The female plug 5 can thereby have the same form for both variants, so that a user can decide in each case whether a wired energy supply and communication is required, or whether the communication should be effected wirelessly and the energy supply provided via the stick, e.g., by means of batteries integrated in the stick. Both the cable and the stick can thereby be used multiple times. In other words, the medico-technical measuring system 1 or the medico-technical measuring device 10 can be provided for one-time use ("disposable"), and, prior to disposal, the cable or the stick can be uncoupled from the female plug.

Figure 6:
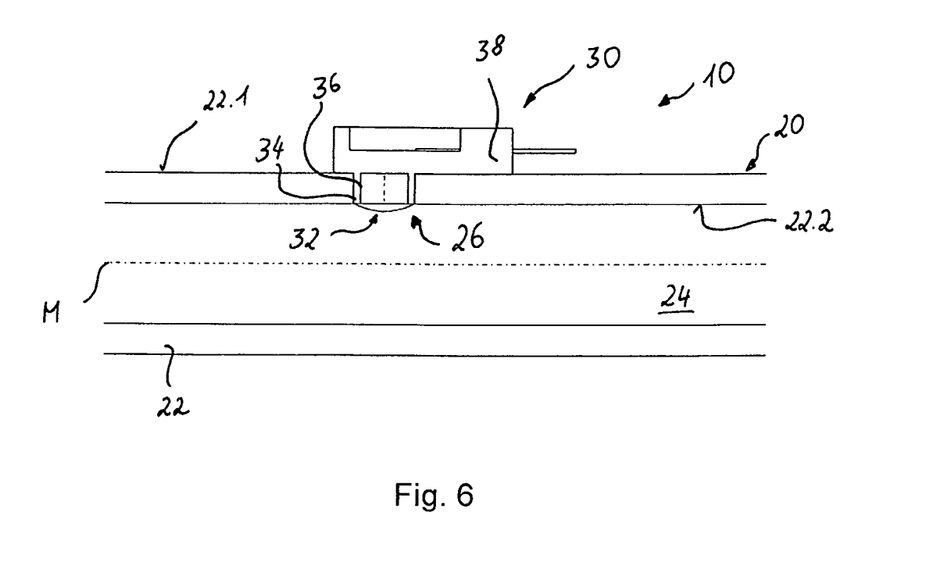
FIG. 6 is a side view in a schematic representation of a sensor unit of a medico-technical measuring device according to one embodiment example of the invention.

FIG. 6 shows a medico-technical measuring device 10 which is assembled comparably to the sensor unit 30 shown in FIG. 2. With this sensor unit 30, the extension of the radial section 36 is adjusted to the wall thickness of the wall 22, such that the sensor 32 is arranged flush with the internal sleeve surface 22.2.

LIST OF REFERENCE SYMBOLS

1 Medico-technical measuring system—in particular, pressure measurement system
3 Adapter cable
5 Female plug
7 Button
9 Extrusion
9.1 Passage in extrusion
10 Medico-technical measuring device
12 Adhesive agent—in particular, glue
14 Cover—in particular, protective cap
16 Membrane
20 Line—in particular, hose line
22 Wall
22.1 External sleeve surface of the wall
22.2 Internal sleeve surface of the wall
24 Longitudinal cavity
26 Radial cavity—in particular, radial opening
26.1 Internal sleeve surface of the radial cavity
30 Sensor unit—in particular, pressure sensor unit
32 Sensor—in particular, pressure sensor
34 Sensor mounting
36 Radial section
38 Abutting section
M Central longitudinal axis
r Radial direction
r22 Wall thickness of the wall

The invention claimed is:
1. A medico-technical measuring device for measuring a pressure of blood, comprising:
a flexible and pliable hose line which extends along a central longitudinal axis and is configured to guide blood within a longitudinal cavity delimited by a wall, the wall having an external sleeve surface and an internal sleeve surface; and
a sensor unit having a radial section with a sensor in the radial section, the sensor configured to measure the pressure of the blood guided in the longitudinal cavity;
wherein the hose line has a radial cavity defined in the wall in a radial direction, the radial cavity extending through the wall from the internal sleeve surface to the external sleeve surface;

the radial section of the sensor unit being at least partially arranged in the radial cavity in a radial position between the external sleeve surface and the internal sleeve surface of the wall and is integrated in the wall, such that the sensor is in communication with the blood;

wherein a diameter or an extent of a cross section of the radial cavity is smaller than the radial section that is at least partially arranged in the radial cavity such that the radial section of the sensor unit forms an oversize fit to which the radial cavity in the wall is sealed in a fluid-tight manner.

2. The measuring device according to claim 1, wherein the measuring device is configured to connect the sensor unit in a single interface with the line to attach it directly to an external sleeve surface of the wall.

3. The measuring device according to claim 1, wherein the sensor is arranged in a radial position between the external sleeve surface and the internal sleeve surface of the wall inside the wall and spaced from the external sleeve surface, wherein the sensor is disposed closer to the internal sleeve surface than to the external sleeve surface.

4. The measuring device according to claim 1, wherein the radial cavity is an opening, the opening being a cylindrical bore with a uniform diameter.

5. The measuring device according to claim 1, wherein the sensor unit is configured to position the sensor in a predefined radial position in the radial cavity.

6. The measuring device according to claim 1, wherein the sensor unit has an abutting section that geometrically corresponds to the external sleeve surface of the wall, at least in an area of the radial cavity and circumferentially around the radial cavity.

7. The measuring device according to claim 6, wherein the sensor unit is partially arranged in the radial cavity in the wall and integrated in the wall such that the sensor is in communication with the fluid and such that the abutting section of the sensor unit lies circumferentially around the radial cavity and to geometrically correspond to the external sleeve surface of the wall.

8. The measuring device according to claim 6, wherein the abutting section of the sensor unit in the area of the radial cavity and circumferentially around the radial cavity is connected substance-to-substance with the external sleeve surface of the wall by means of an adhesive agent.

9. The measuring device according to claim 1, wherein the radial section of the sensor unit has an extension in a radial direction, the extension being larger than half of a wall thickness of the wall of the line in a section in which the radial cavity is arranged.

10. The measuring device according to claim 9, wherein at least the radial section of the sensor unit is formed from a plastic material.

11. The measuring device according to claim 1, wherein the measuring device is a disposable device provided for one-time use, wherein the sensor unit has a coupling point for a transmission by wire over a cable or for a wireless transmission.

12. The measuring device according to claim 1, wherein at least two measuring devices are further incorporated in a measuring system, wherein one of the measuring devices has a feed line, and the other of the measuring devices has a discharge line.

13. The measuring device according to claim 1, wherein the diameter or the extent of the cross section of the radial cavity is constant from the internal sleeve surface to the external sleeve surface.

14. A method for assembling a medico-technical measuring device for measuring a pressure of blood, comprising the steps of:

providing a flexible and pliable hose line with a wall, the hose line extending along a central longitudinal axis and configured to guide blood within a longitudinal cavity delimited by the wall, the wall having an external sleeve surface and an internal sleeve surface;

inserting a radial cavity in the wall in a radial direction, the radial cavity extending through the wall from the internal sleeve surface to the external sleeve surface; and arranging a sensor at least partially in the radial cavity and in a radial position between the external sleeve surface and the internal sleeve surface of the wall such that the sensor is in communication with the blood;

wherein a diameter or an extent of a cross section of the radial cavity is smaller than the sensor that is at least partially arranged in the radial cavity such that the sensor forms an oversize fit to which the radial cavity in the wall is sealed in a fluid-tight manner.

15. The method according to claim 14, wherein the measuring device is connected substance-to-substance with an external sleeve surface of the wall.

16. A method for measuring a pressure of blood by means of a medico-technical measuring device, comprising the steps of:

guiding the blood through a line within a longitudinal cavity delimited by a wall;

measuring the pressure of the blood by means of a sensor of the measuring device;

wherein the pressure of the blood is measured in a radial cavity inserted in the wall in which the sensor is at least partially positioned, the radial cavity extending from an internal sleeve surface to an external sleeve surface of the wall;

wherein the sensor is positioned in a radial position between the external sleeve surface and the internal sleeve surface of the wall distanced from the external sleeve surface and in a radial position closer to the internal sleeve surface than to the external sleeve surface, and a diameter or an extent of a cross section of the radial cavity is smaller than the sensor that is at least partially arranged in the radial cavity such that the sensor forms an oversize fit to which the radial cavity in the wall is sealed in a fluid-tight manner.

* * * * *